United States Patent [19]

Roberts et al.

[11] Patent Number: 5,171,748

[45] Date of Patent: Dec. 15, 1992

[54] BENZ[4,5]IMIDAZOLE-CONTAINING ANGIOTENSIN ANTAGONISTS

[75] Inventors: David A. Roberts, Congleton; Simon T. Russell, Macclesfield, both of United Kingdom

[73] Assignee: Imperial Chemical Industries plc, London, England

[21] Appl. No.: 526,861

[22] Filed: May 22, 1990

[30] Foreign Application Priority Data

May 23, 1989 [GB] United Kingdom ............ 8911854

[51] Int. Cl.$^5$ ............ A61K 31/41; A61K 31/415; C07D 257/04; C07D 235/08
[52] U.S. Cl. ............ 514/381; 514/394; 548/101; 548/252; 548/254; 548/310.7; 548/304.4
[58] Field of Search ............ 548/325, 252, 254, 101; 514/381, 394

[56] References Cited

U.S. PATENT DOCUMENTS

| | | | |
|---|---|---|---|
| 4,612,323 | 9/1986 | Kisida et al. | 514/394 |
| 4,663,339 | 5/1987 | Kisida et al. | 514/394 |
| 4,820,843 | 4/1989 | Aldrich et al. | 548/252 |
| 4,859,692 | 8/1989 | Bernstein et al. | 514/381 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |
| 5,051,530 | 9/1991 | Chang et al. | 560/184 |

FOREIGN PATENT DOCUMENTS

| | | |
|---|---|---|
| 0132606 | 2/1985 | European Pat. Off. . |
| 0186190 | 7/1986 | European Pat. Off. . |
| 0253310 | 1/1988 | European Pat. Off. . |
| 0291969 | 11/1988 | European Pat. Off. . |
| 0323841 | 7/1989 | European Pat. Off. . |
| 0392317 | 10/1990 | European Pat. Off. . |
| 0400835 | 12/1990 | European Pat. Off. . |
| 0420237 | 5/1991 | European Pat. Off. . |
| 0425921 | 5/1991 | European Pat. Off. . |

OTHER PUBLICATIONS

Sinkula, A. A. "Prodrug Approach in Drug Design" In *Ann. Rep. Med. Chem.* (1975), 10, 306–316.

Stella, V. "Pro-drugs: An Overview and Definition" and Sinkula, A. A. "Application of the Pro-drug Approach to Antibiotics" In *Pro-Drugs as Novel Drug Delivery Systems;* Higuchi, T. and Stella V. Eds.; ACS Symposium Series 14, American Chemical Society: Washington, DC, 1975; pp. 1–15, 44–45, 116–153.

Bundgaard, H. "Design of prodrugs: Bioreversible derivatives for various functional groups and chemical entities" In *Design of Prodrugs;* Bundgaard, H., Ed.; Elsevier Science Publishers: Amsterdam, 1985; pp. 1–10.

Bundgaard, H., "Design of Bioreversible Drug Derivatives and the Utility of the Double Prodrug Concept" In *Bioreversible Carriers in Drug Design;* Roche, E. B., Ed.; Pergamon Press: New York, 1987; pp. 13–21.

*Primary Examiner*—Robert W. Ramsuer
*Assistant Examiner*—Michael G. Ambrose
*Attorney, Agent, or Firm*—Thomas E. Jackson

[57] ABSTRACT

The invention concerns novel heterocyclic compounds of the formula I as defined herein and their physiologically acceptable salts, together with pharmaceutical compositions containing them. The heterocyclic compounds antagonize the actions of angiotensin II and are of value in treating diseases or medical conditions such as hypertension and congestive heart failure in warm-blooded animals. The invention further includes processes for the manufacture of the novel compounds and their use in medical treatment.

12 Claims, No Drawings

BENZ[4,5]IMIDAZOLE-CONTAINING ANGIOTENSIN ANTAGONISTS

This invention concerns novel heterocyclic compounds and, more particularly, novel benzimidazole derivatives which possess pharmacologically useful properties in antagonising at least in part one or more of the actions of the substances known as angiotensins, and in particular of that known as angiotensin II (hereafter referred to as AII). The invention also concerns pharmaceutical compositions of the novel compounds for use in treating diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The invention also includes processes for the manufacture of the novel compounds and their use in treating one of the afore-mentioned diseases or medical conditions and for the production of novel pharmaceuticals for use in such medical treatments.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) from angiotensin I, itself produced by the action of the enzyme renin from the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Hitherto there have been a number of different approaches to pharmacological intervention in the renin-angiotensin-aldosterone system for therapeutic control of blood pressure and/or fluid/electrolyte balance, including, for example, inhibiting the actions of renin or ACE. However, there remains a continuing need for an alternative approach because of the side-effects and/or idiosyncratic reactions associated with any particular therapeutic approach.

Certain substituted imidazoles described in European Patent Application, publication No. 253310 A2 are known to inhibit the action of angiotensin II.

We have now discovered that the compounds of the invention (set out below) surprisingly antagonise one or more of the actions of the substances known as angiotensins (and in particular of AII) and thus minimise the physiological effects associated with their presence in warm-blooded animals (including man) and this is the basis of the invention.

According to the invention there is provided a benzimidazole derivative of the formula I (set out hereinafter, together with the other chemical formulae identified by Roman numerals) wherein $R^1$ is (1–8C)alkyl, (3–8C)cycloalkyl, (3–8C)cycloalkyl-(1–4C)alkyl, phenyl or phenyl(1–4C)alkyl; $R^2$ is hydrogen, (1–4C)alkyl, (1–4C)alkoxy, halogeno, trifluoromethyl, cyano or nitro; $R^3$ and $R^4$ are independently selected from hydrogen, (1–4C)alkyl, (1–4C)alkoxy, halogeno, trifluoromethyl, cyano and nitro; X is phenylene optionally bearing a substituent selected from (1–4C)alkyl, (1–4C)alkoxy and halogeno, or X is a direct bond between the adjacent phenyl and methylene moieties; and Z is 1H-tetrazol-5-yl or a group of the formula $-CO.OR^5$ or $-CO.NH.SO_2.R^6$ in which $R^5$ is hydrogen or a non-toxic, biodegradable residue of a physiologically acceptable alcohol or phenol, and $R^6$ is (1–6C)alkyl, (3–8C)cycloalkyl or phenyl; and wherein any of said phenyl moieties may be unsubstituted or bear one or two substituents independently selected from (1–4C)alkyl, (1–4C)alkoxy, halogeno, cyano and trifluoromethyl; or a physiologically acceptable salt thereof except when $R^5$ is other than hydrogen.

It will appreciated that, depending on the nature of the substituents, certain of the formula I compounds may possess one or more chiral centres and may be isolated in one or more racemic or optically active forms. It is to be understood that this invention concerns any form of such a compound of formula I which possesses the afore-mentioned useful pharmacological properties, it being well known how to make optically active forms, for example by synthesis from suitable chiral intermediates, and how to determine their pharmacological properties, for example by use of the standard tests described hereinafter.

It is to be understood that generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

A particular value for $R^1$ when it is alkyl is, for example, methyl, ethyl, propyl, butyl, isobutyl, sec-butyl, pentyl or hexyl; when it is cycloalkyl is, for example, cyclopropyl, cyclopentyl or cyclohexyl; when it is cycloalkyl-alkyl is, for example, cyclopropylmethyl, cyclopentylmethyl, cyclohexylmethyl or 2-cyclopentylethyl; and when it is phenylalkyl is, for example, benzyl, 1-phenylethyl or 2-phenylethyl.

Particular values for $R^2$, $R^3$, $R^4$ or an optional substituent which may be present when X is phenylene, include, by way of example: when it is alkyl, methyl and ethyl; when it is alkoxy, methoxy and ethoxy; and when it is halogeno, fluoro, chloro, bromo and iodo.

A particular value for $R^5$ when it is a non-toxic, biodegradable residue of a physiologically acceptable alcohol or phenol is, for example, a residue derived from a (1–6C)alkanol such as methanol or ethanol, or phenol, glycerol or the like.

A particular value for $R^6$ when it is alkyl is, for example, methyl, ethyl, propyl, isopropyl, butyl or pentyl; and when it is cycloalkyl is, for example, cyclobutyl, cyclopentyl or cyclohexyl.

Particular values for optional substituents which may be present on phenyl moieties include, by way of example, for halogeno, fluoro, chloro and bromo; for alkyl, methyl or ethyl; and for alkoxy, methoxy and ethoxy.

Specific values for X which are of particular interest include, for example, when it is a direct bond or p-phenylene.

A preferred value for $R^5$ is, for example, hydrogen and for $R^1$ is, for example, butyl.

A preferred group of compounds comprises benzimidazole derivatives of the formula I wherein $R^1$ is (1–8C)alkyl; $R^2$ is hydrogen, (1–4C)alkyl, halogeno or nitro; $R^3$ and $R^4$ are independently selected from hydrogen, halogene and trifluoromethyl; X is a direct bond or p-phenylene; and Z is selected from 1H-tetrazol-5-yl, carboxy and a group of the formula $-\overline{C}O.NH.SO_2.R^6$ in which $R^6$ has any of the meanings defined above, and wherein Z is attached at the 2- or 4-position relative to X.

Compounds of the invention which are of particular interest include, for example, the specific embodiments set out hereinafter in the accompanying Examples.

Particularly suitable salts of compounds of formula I include, for example, for acidic compounds, salts with bases affording physiologically acceptable cations, for example, alkali metal (such as sodium and potassium), alkaline earth metal (such as magnesium and calcium), aluminium and ammonium salts, as well as salts with suitable organic bases, such as with ethanolamine, methylamine, diethylamine or triethylamine.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise.

a) For those compounds in which Z is carboxy (that is in which Z is a group of the formula —$CO.OR^5$ in which $R^5$ is hydrogen), a carboxylic acid derivative of the formula II, in which Q is a protected carboxy group selected from (1-6C)alkoxycarbonyl (especially methoxy-, ethoxy-, propoxy- or t-butoxy-carbonyl), phenoxycarbonyl, benzyloxycarbonyl and carbamoyl, is converted to carboxy.

The conversion may be carried out, for example by hydrolysis, conveniently in the presence of a suitable base such as an alkali metal hydroxide, for example, lithium, sodium or potassium hydroxide. The hydrolysis is generally carried out in the presence of a suitable aqueous solvent or diluent, for example in an aqueous (1-4C)alkanol, such as aqueous methanol or ethanol. However, it may also be performed in a mixture of an aqueous and non-aqueous solvent such as water and toluene using a conventional quaternary ammonium phase tranfer catalyst. The hydrolysis is generally performed at a temperature in the range, for example, 0°-120° C., depending on the reactivity of the group Q. In general, when Q is carbamoyl, temperatures in the range, for example, 40°-120° C. are required to effect the hydrolysis.

Alternatively, when Q is benzyloxycarbonyl, the conversion may also be performed by hydrogenolysis, for example using hydrogen at 1-3 bar in the presence of a suitable catalyst, such as palladium on charcoal or on calcium sulphate, in a suitable solvent or diluent such as a (1-4C)alkanol (typically ethanol or 2-propanol) and at a temperature in the range, for example, 0°-40° C.

Further, when Q is t-butoxycarbonyl, the conversion may also be carried out by hydrolysis at a temperature in the range, for example, 0°-100° C., in the presence of a strong acid catalyst, such as trifluoroacetic acid. The hydrolysis may either be performed in an excess of the acid or in the presence of a suitable diluent such as tetrahydrofuran, t-butyl methyl ether or 1,2-dimethoxyethane.

b) For those compounds of formula I wherein Z is tetrazolyl, a compound of the formula III in which L is a suitable protecting group, such as trityl, benzhydryl, trialkyltin (for example trimethyltin) or triphenyltin, affixed to a nitrogen of the tetrazolyl moiety, is deprotected.

The reaction conditions used to carry out the deprotection necessarily depend on the nature of the group L. As an illustration, when it is trityl, benzhydryl, trialkyltin or triphenyltin, the decomposition conditions include, for example, acid catalysed hydrolysis in a mineral acid (such as aqueous hydrochloric acid), conveniently in an aqueous solvent (such as aqueous dioxan or 2-propanol). Alternatively, a trityl or benzhydryl group may be removed by hydrogenolysis, for example as described in (a) above for conversion of a benzyloxycarbonyl to a carboxy.

Compounds of the formula III wherein L is trialkyltin or triphenyltin may be obtained, for example, by reaction of a nitrile of formula IX with a trialkyltin, such as trimethyltin, or triphenyltin respectively. The reaction is conveniently carried out in a suitable solvent or diluent, such as toluene or xylene, and at a temperature in the range 50°-150° C. It will be appreciated that the use of suitable work-up conditions, for example acidic work-up conditions, may enable compounds of the formula I wherein Z is tetrazole to be obtained directly without prior isolation of the protected tetrazole. The nitriles of formula IX may be obtained, for example, by alkylation of an benzimidazole derivative of the formula IV with a nitrile of the formula X wherein Hal. stands for a suitable leaving group such as chloro, bromo, iodo, methanesulphonyloxy or p-toluenesulphonyloxy, using similar conditions to those used in process (c) described hereinafter. The necessary compounds of the formula IX may be made by standard procedures such as that illustrated in Scheme 1 for compounds in which X is phenylene.

c) Reacting a benzimidazole of the formula IV with a compound of the formula V wherein Hal. stands for a suitable leaving group such as chloro, bromo, iodo, methanesulphonyloxy of p-toluenesulphonyloxy.

The reaction is generally carried out in the presence of a suitable base, for example, an alkali metal carbonate such as potassium carbonate or an organic base such as diisopropylethylamine and in a suitable solvent or diluent, for example in a polar solvent such as dimethylformamide and at a temperature in the range, for example, 10°-80° C.

Procedure (c) is particularly suitable for the production of those compounds of the formula I in which Z is a group of the formula —$CO.OR^5$ in which $R^5$ is other than hydrogen, for example wherein $R^5$ is (1-6C)alkyl, benzyl or phenyl, which compounds are also starting materials of formula II for the reaction described in (a) above. Similarly, using an analogous procedure, but starting with the appropriate compound of the formula VI, the starting materials of the formula III may be obtained for procedure (b). In this context, it will be appreciated that when one or both of the substituents $R^3$ and $R^4$ in the required compound of formula I are other than hydrogen and are located asymmetrically in the benzene moiety relative to the imidazole nitrogen atoms, two positional isomeric compounds of formula II or III may be obtained during alkylation of the benzimidazole of formula IV with the compound of formula V and VI respectively. Such positional isomers may be separated by conventional procedures such as fractional crystallisation or chromatography.

The majority of the benzimidazoles of formula IV are already known and the remainder can be made by analogy therewith using standard procedures of organic chemistry well known in the art, for example as described in standard works of heterocyclic chemistry such as that edited by Elderfield. The necessary compounds of the formula V (and also of formula VI) may be made by standard procedures such as those which are illustrated in Scheme 1 for compounds in which X is phenylene.

(d) Reacting a 1,2-diaminobenzene derivative of the formula VII with a carboxylic acid of the formula $R^1.CO_2H$ or a (1–4C)alkyl orthoester (for example the methyl or ethyl orthoester) thereof. When the acid $R^1.CO_2H$ is used, the reaction is generally performed in the presence of a dehydrating agent. Particularly suitable dehydrating agents include, for example, polyphosphoric acid and lower alkyl esters thereof, for example, the ethyl ester thereof.

The reaction may be performed in the absence of solvent or conveniently in the presence of an excess of the carboxylic acid of formula $R^1.CO_2H$ or of an orthoester thereof. The reaction is usually performed at an elevated temperature, for example in the range 40°–150° C.

It will be appreciated that an intermediate frequently obtained in the reaction is an alkanoylamino compound of the formula VIII, formed by initial acylation of the primary amino group. This compound of formula VIII may be separately formed, for example, by reaction of the compound of formula VII with the acid chloride, bromide or anhydride of those alkanoic acids of formula $R^1.CO_2H$ in which $R^1$ is other than hydrogen, generally in the presence of a suitable base such as triethylamine at a temperature in the range, for example, 0°–50° C. Those compounds of formula VII wherein $R^1$ is hydrogen may be obtained, for example, by heating the diamino compound of formula VII with formic acid or triethylorthoformate at a temperature in the range, for example, 40°–100° C. The alkanoylamino compound of formula VIII may then be cyclised by heating with a suitable dehydrating agent as described for process (d) above.

Whereafter, those compounds of the formula I wherein Z is a group of the formula $-CO.NH.SO_2R^6$ or a group of the formula $-CO.OR^5$ in which $R^5$ is other than hydrogen, may be obtained, for example, by reacting a carboxylic acid of the formula I in which Z is carboxy (or a reactive derivative of said acid) with a sulphonamide of the formula $NH_2.SO_2R^6$ or a hydroxy compound of the formula $HO.R^5$, or with a salt thereof (for example, an alkali metal thereof). Suitable reactive derivatives include, for example the chloride, bromide, azide, anhydride and mixed anhydride with formic or acetic acid of the carboxylic acid of formula I as defined above. When the free acid form is used, the reaction is generally carried out in the presence of a suitable dehydrating agent such as dicyclohexycarbodiimide or 3-(3-dimethylaminopropyl)-1-ethylcarbodiimide in the presence of a base such as triethylamine or pyridine. When a reactive derivative is used, either the reaction is carried out in the presence of a base such as mentioned above, or the sulphonamide or hydroxy compound is used in the form of a salt, such as its alkali metal salt (in particular the lithium, sodium or potassium salt thereof). The reaction is generally performed in the presence of a suitable diluent or solvent such as dioxan, t-butyl methyl ether or tetrahydrofuran and at a temperature in the range, for example, 0°–60° C.

Whereafter, when a salt of a compound of formula I is required, it may be obtained, for example, by reaction with the appropriate base affording a physiologically acceptable cation, or by any other conventional salt formation procedure.

Further, when an optically active form of a compound of formula I is required, one of the aforesaid processes may be carried out using an optically active starting material. Alternatively, the racemic form of a compound of formula I in which Z is an acidic group may be resolved, for example by reaction with an optically active form of a suitable organic base, for example, ephedrine, N,N,N-trimethyl-(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid.

Certain of the intermediates defined herein are novel, for example the compounds of the formula II, III and VII, and are provided as a further feature of the invention.

As stated above, the compounds of formula I will have beneficial pharmacological effects in warm-blooded animals (including man) in diseases and medical conditions where amelioration of the vasoconstrictor and fluid retaining properties of the reninangiotensin-aldosterone system is desirable, at least in part by antagonism of one or more of the physiological actions of AII. The compounds of the invention will thus be useful in the treatment of diseases or medical conditions such as hypertension, congestive heart failure and/or hyper-aldosteronism in warm-blooded animals (including man), as well as in other diseases or medical conditions in which the renin-angiotensin-aldosterone system plays a significant causative role.

The antagonism of one or more of the physiological actions of AII and, in particular, the antagonism of the interaction of AII with the receptors which mediate its effects on a target tissue, may be assessed using one or more of the following, routine laboratory procedures.

Test A: This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^{-4}$ M are retested at lower concentrations to determine their potency. For determination of the $IC_{50}$ (concentration for 50% displacement of radiolabelled AII binding), concentrations of the test compound are ordinarily chosen to allow testing over at least four orders of magnitude centred about the predicted approximate $IC_{50}$, which latter is subsequently determined from a plot of percentage displacement against concentration of the test compound.

In general, acidic compounds of formula I as defined above show significant inhibition in Test A at a concentration of 50 micromolar or much less.

Test B: This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, acidic compounds of formula I as defined above show significant inhibition in Test B at a final concentration of 50 micromolar or much less. [Note: Non-acidic compounds of formula I (that is those compounds wherein Z is a group of the formula —$CO.OR^5$ in which $R^5$ is other than hydrogen) in general show only weak activity in the in vitro Tests A or B.]

Test C: This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against angiotensin II-induced pressor responses. To ensure that the effect is specific the effect of the test compound on vasopressin-induced pressor responses may also be determined in the same preparation.

The compounds of formula I generally show specific AII-antagonist properties in Test C at a dose of 50 mg/kg body weight or much less, without any overt toxicological or other untoward pharmacological effect.

Test D: This in vivo involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been implanted under anaesthesia for the measurement of changes in blood pressure.

In general compounds of formula I will show AII-antagonist properties in Test D as demonstrated by a significant reduction in blood pressure at a dose of 50 mg/kg body weight or much less, without any overt toxicological or other untoward pharmacological effect.

The compounds of formula I will generally be administered for therapeutic or prophylactic purposes to warm-blooded animals (including man) requiring such treatment in the form of a pharmaceutical composition in conjunction with a pharmaceutically acceptable diluent or carrier, as is well known in the pharmaceutical art. Such a pharmaceutical composition is provided as a further faeture of the invention and will conveniently be in a form suitable for oral administration (e.g. as a tablet, capsule, solution, suspension or emulsion) or parenteral administration (e.g. as an injectable aqueous or oily solution, or injectable emulsion).

The compounds of formula I may also be advantageously administered for therapeutic or prophylactic purposes together with another pharmacological agent known in the general art to be of value in treating one or more of the diseases or medical conditions referred to hereinabove.

In general a compound of formula I (or a pharmaceutically acceptable salt thereof as appropriate) will generally be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

By way of illustration of the angiotensin II inhibitory properties of compounds of formula I, the compound of Example 3 gave the following results in tests A, B and C described above:

In test A: $IC_{50}$ of $1 \times 10^{-7}M$;
In test B: $pA_2$ of 7.6;
In test C: $ED_{50}$ of 3 mg/kg (parenteral administration).

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of AII in laboratory animals such as cats, dogs, rabbits, monkeys, rats and mice, as part of the continuing search for new and improved therapeutic agents.

The invention will now be illustrated by the following non-limiting Examples in which, unless otherwise stated:

(i) concentrations and evaporations were carried out by rotary evaporation in vacuo;

(ii) operations were carried out at room temperature, that is in the range 18°-26° C.;

(iii) flash column chromatography was performed on Merck Kieselgel 60 (Art. no. 9385) obtained from E Merck, Darmstadt, Germany;

(iv) yields, where given, are intended for the assistance of the reader only and are not necessarily the maximum attainable by diligent process development;

(v) proton NMR spectra were normally determined at 200 MHz in $CDCl_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; and (vi) all end-products had satisfactory microanalyses.

EXAMPLE 1

1M Aqueous sodium hydroxide solution (6.5 ml) was added to a solution of methyl 4'-[(2-butyl-1H-benzimidazol-1-yl)methyl]biphenyl-2-carboxylate ($\overline{A}$) (2.0 g) in ethanol (20 ml). The solution was heated under reflux for 3 hours and then volatile material was removed by evaporation. The residue was dissolved in water (20 ml) and the solution acidified to pH 4 with 20% aqueous citric acid. The precipitated solid was collected and dried under high vacuum to give 4'-[(2- butyl-1H-benzimidazol-1-yl)methyl]biphenyl-2-carboxylic acid (0.83 g), as a white powder, m.p. 225°-227° C.; NMR (d$_6$-DMSO): 0.9(t,3H), 1.4(m,2H), 1.7(m,2H), 2.85(t,3H), 5.5(s,2H), 7.15(m,4H), 7.3(m,3H), 7.4-7.7 (complex m,5H); 12.6(br, 1H); mass spectrum (positive chemical ionisation; hereinafter referred to as "+ve CI"): 385 (M+H)+, 384 (M+), 355, 342, 298, 211, 165, 145, 132, 77; microanalysis found: C,77.2; H,6.5; N,7.0; C$_{25}$H$_{25}$N$_2$.025 H$_2$O requires: C,77.2; H,6.2; N,7.2%.

The starting material (A) was obtained as follows:

(i) A 1.6M solution of butyllithium in hexane (24.4 ml) was added dropwise to a stirred solution of 4-bromotoluene (6.0 g) in dry tetrahydrofuran (THF, 50 ml) at −78° C. under an atmosphere of argon. The temperature was maintained at −78° C. for 20 minutes, and then a 1M solution of anhydrous zinc chloride in ether (38.6 ml) was added. The solution was kept at −78° C. for 15 minutes and then tetrakis(triphenylphosphine)palladium (60 mg) in THF (5 ml) was added, followed by methyl 2-iodobenzoate (6.1 g) in THF (10 ml). The solution was allowed to reach ambient temperature over 1 hour, then heated under reflux for 5 hours. The solvent was removed by evaporation and the residue was dissolved in chloroform (150 ml). The solution washed with a solution of ethylenediaminetetracetic acid (10 g) in water (100 ml) and the aqueous layer was re-extracted with chloroform (100 ml). The combined organic extracts were dried (MgSO$_4$) and the solvent removed by evaporation. The residue was purified by flash chromatography, eluting with ethyl acetate/hexane (1:9 v/v), to give methyl 4'-methylbiphenyl-2-carboxylate (B) as a colourless oil (4.4 g); NMR (CDCl$_3$): 2.4(s,3H), 3.65(s,3H), 7.2(s,4H), 7.35(m,3H), 7.35(m,3H), 7.5(m,1H), 7.8(d,1H).

(ii) N-Bromosuccinimide (8.1 g) and azo(-bisisobutyronitrile) (130 mg) were added to a solution of compound (B) (9.3 g) in carbon tetrachloride (300 ml). The mixture was heated under reflux for 4 hours and then cooled to ambient temperature. Insoluble material was removed by filtration and the filtrate concentrated. The residue was purified by flash chromatography, eluting with ethyl acetate/hexane (1:9 v/v) to give methyl 4'-(bromomethyl)biphenyl-2-carboxylate (C) as a solid (10.9 g), m.p. 48°-50° C.; NMR (CDCl$_3$) 3.65(s, 3H), 4.55(s,2H), 7.25-7.60 (complex m,7H), 7.85(d,1H).

(ii) A mixture of 2-butylbenzimidazole (2.6 g), the bromomethyl compound (C) (5.0 g) and potassium carbonate (1.55 g) in N,N-dimethylformamide (DMF) (40 ml) was heated at 100° C. for 3 hours. Dichloromethane (200 ml) was added and insoluble material was removed by filtration. The filtrate was concentrated and the residue purified by flash chromatography, eluting with triethylamine/ethyl acetate/hexane (1:40:60 v/v/v), to give methyl 4'-[2-butyl-1H-benzimidazol-1-yl)methyl]-biphenyl-2-carboxylate (A) as a clear oil (2.7 g); NMR (CDCl$_3$): 0.95(t,3H), 1.45(m,2H), 2.9(t,2H), 3.6(s,3H), 5.4(s,2H), 7.2(d,2H), 7.2-7.6 (complex m,3H), 7.8(m,2H).

EXAMPLE 2

Using an analogous procedure to that described in Example 1, except that the reaction was performed at ambient temperature, methyl 4-[(2-butyl-1H-benzimidazol-1-)methyl]benzoate (D) (320 mg) was hydrolysed to give 4-[(2-butyl-1H-benzimidazol-1-yl)methyl]-benzoic acid (127 mg), as fine white needles, m.p. 229°-231° C. (from aqueous methanol); NMR (d$_6$-DMSO): 0.85(t,3H, 1.35(m,2H), 1.7(m,2H), 2.8(t,3H), 5.55(s,2H), 7.15(m,4H), 7.4(m,1H), 7.6(m,1H), 7.9(d,1H), 12.9(br,1H); mass spectrum [(negative fast atom bombardment, hereinafter referred to as "−ve FAB"), DMSO/glycerol]: 307 (M−H)−, 173; microanalysis found: C,73.1; H,6.5; N,8.5; C$_{19}$H$_{20}$N$_2$O$_2$.0.25-H$_2$O requires: C,73.0; H,6.6; N,9.0%.

The starting material (D) was obtained as follows:

Using an analogous procedure to that described in Example 1 for compound A, but starting from ethyl 4-bromomethylbenzoate (368 mg) and proportionate quantities of other necessary reagents, there was obtained, after flash chromatography eluting with ethyl acetate/hexane (1:1 v/v), methyl 4'-[(2-butyl-1H-benzimidazol-1-yl)methyl]benzoate (D) as a colourless oil (320 mg); NMR (CDCl$_3$): 0.9(t,3H), 1.4(m,2H), 1.7(m,2H), 2.8(t,2H), 3.9(s,3H), 5.4(s,2H), 7.1-7.3 (complex m,5H), 7.8(d,1H), 8.0(d,2H).

EXAMPLE 3

4-[(2-Butyl-1H-benzimidazol-1-yl)methyl]benzoic acid (150 mg) was added to a solution of benzenesulphonamide (79 mg), dimethylaminopyridine (60 mg) and 1-[3-(dimethylamino)propyl]-3-ethylcarbodiimide hydrochloride (91 mg) in dry dichloromethane (5 ml). The mixture was stirred overnight and then diluted with dichloromethane (20 ml). The solution was washed successively with 1M hydrochloric acid (20 ml), water (20 ml) and saturated brine (20 ml), and then dried (MgSO$_4$). The solvent was removed by evaporation and the residue triturated with ether to give 4-[(2-butyl-1H-benzimidazol-1-yl)methyl]-N-phenylsulphonylbenzamide as a white solid, m.p. 241°-242° C.; NMR (d$_6$-DMSO): 0.9(t,3H), 1.35(m,2H), 1.7(m,2H), 2.85(t,2H), 5.6(s,2H), 7.2(m,3H), 7.4(m,1H), 7.6(m,4H). 7.8(d,2H), 8.0(d,2H); mass spectrum (−ve FAB, DMSO/m-nitrobenzyl alcohol): 446(M−H)−; microanalysis found: C,66.7; H,5.6; N,9.1; C$_{25}$H$_{25}$N$_3$O$_3$S requires: C,67.1; H,5.6; N,9.4%.

EXAMPLE 4

2-Butyl-1-[(2'-(2-triphenylmethyl-2H-tetrazol-5-yl)biphenyl-4-yl)methyl]benzimidazole (E) (400 mg) was dissolved in an 8M solution of hydrogen chloride in dioxan (5 ml) and water (0.5 ml) was added. The solution was allowed to stand for 1.5 hours and then volatile material was removed by evaporation. The residue was partitioned between sodium hydrogen carbonate solution (10 ml) and ether (10 ml). The aqueous phase was separated, washed with ether (3×10 ml) and acidified to pH4 with 20% aqueous citric acid. The precipitated solid was collected and recrystallised from ethyl acetate to give 2-butyl-1-[(2'-(1H-tetrazol-5-yl)biphenyl-4-yl)methyl]benzimidazole (94 mg), as white crystals, m.p. 230°-232° C.; NMR (d$_6$-DMSO): 0.88(t,3H), 1.35(m,2H), 1.7(m,2H), 2.8(t,2H), 5.5(s,2H), 7.0(s,4H), 7.15(m,2H), 7.4-7.7 (complex, 6H); mass spectrum (−ve FAB, DMSO/NBA): 407 (M−H)−, 379; microanalysis found: C,73.7; H,6.2; N,20.8; C$_{25}$H$_{24}$N$_6$ requires: C,73.5; H,5.9; N,20.6%.

The starting material (E) was obtained as follows:

Using an analogous procedure to that described in Example 1 for compound C, but starting from 5-[2-(4'-bromomethylbiphenylyl)]-2-triphenylmethyl-2H-tetrazole (836 mg) (obtained as described in European Patent 0291969) and proportionate quantities of other necessary reagents, and extending the reaction time to 8 hours, there was obtained, after flash chromatography eluting with ethyl acetate/hexane (1:1 v/v), 2-butyl-1-

[(2'-(2-triphenylmethyl-2H-tetrazol-5-yl)biphenyl-4-yl)methyl]-benzimidazole (E) (425 mg) as a white foam, m.p. 74°–78° C.; NMR (CDCl$_3$): 0.9(t,3H), 1.4(m,2H), 1.8(m,2H), 2.8(t,2H), 5.2(s,2H), 6.8(d,2H), 6.9(d,6H), 7.1(m,4H), 7.1–7.4 (complex m,11H), 7.5(m,2H), 7.8(d,1H), 7.9(m,1H).

EXAMPLES 5–7

The following compounds were obtained using an analogous procedure to that described in Example 2 in yields ranging from 47–75%:

(Example 5): 4-[(2-butyl-1H-benzimidazol-1-yl)methyl]-2-bromobenzoic acid, as a white solid, m.p. 207°–208° C. (from aqueous methanol); NMR (d$_6$-DMSO): 0.87(t, 3H), 1.36(m, 2H), 1.70(m, 2H), 2.82(t, 2H), 5.55(s, 2H), 7.04(dd, 1H), 7.1–7.2(complex m, 2H), 7.4–7.5(complex m, 2H), 7.59(dd, 1H), 7.70(d, 1H); mass spectrum (+ve CI): 387(M+H)$^+$, 309, 175; microanalysis found: C, 59.0; H, 4.9; N, 7.2; C$_{19}$H$_{19}$BrN$_2$O$_2$ requires: C, 58.9; H, 4.9; N, 7.2%;

(Example 6): 4-[(2-butyl-1H-benzimidazol-1-yl)methyl]-3-bromobenzoic acid, as a white solid, m.p. 242°–244° C. (from aqueous methanol); NMR (d$_6$-DMSO): 0.85(t, 3H), 1.34(m, 2H), 1.68(m, 2H), 2.76(t, 2H), 5.56(s, 2H), 6.46(d, 1H), 7.1–7.25(complex m, 2H), 7.35(dd, 1H), 7.63(dd, 1H), 7.78(dd, 1H), 8.18(dd, 1H), 13.2(br s, 1H); mass spectrum (+ve CI): 387(M+H)$^+$, 344, 265, 175; microanalysis found: C, 58.6; H, 4.8; N, 7.0; C$_{19}$H$_{19}$BrN$_2$O$_2$ requires: C, 58.9; H, 4.9; N, 7.2%; and (Example 7): 4-[(2-butyl-1H-benzimidazol-1-yl)methyl]-3-nitrobenzoic acid, as a white solid, m.p. 225°–228° C. (from aqueous methanol); NMR (d$_6$-DMSO): 0.85(t, 3H), 1.36(m, 2H), 1.73(m, 2H), 2.78(t, 2H), 5.93(s, 2H), 6.46(d, 1H), 7.17(m, 2H), 7.40(dd, 1H), 7.63(dd, 1H), 8.08(dd, 1H), 8.64(d, 1H), 13.5(br s, 1H); mass spectrum (−ve FAB, DMSO/glycerol): 352(M−H)$^-$, 173: microanalysis found: C, 63.8; H, 5.4; N, 11.8; C$_{19}$H$_{19}$N$_3$O$_4$.0.25H$_2$O requires: C, 63.8; H, 5.4; N, 11.7%.

The following starting materials were obtained using an analogous procedure to that described in Example 1, part (iii), in yields ranging from 29–67%:

(Example 5A): Methyl 4-[(2-butyl-1H-benzimidazol-1-yl)methyl]-2-bromobenzoate, as an oil; NMR (CDCl$_3$): 0.94(t, 3H), 1.45(m, 2H), 1.84(m, 2H), 2.81(t, 2H), 3.92(s, 3H), 5.35(s, 2H), 6.93(dd, 1H), 7.14(d, 1H), 7.21(t, 1H), 7.26(t, 1H), 7.43(s, 1H), 7.72(d, 1H), 7.78(d, 1H);

(Example 6A): Methyl 4-[(2-butyl-1H-benzimidazol-1-yl)methyl]-3-bromobenzoate, as a white solid; m.p. 150°–152° C.; NMR (CDCl$_3$): 0.92(t, 3H), 1.43(m, 2H), 1.83(m, 2H), 2.80(t, 2H), 3.91(s, 3H), 5.40(s, 2H), 6.45(d, 1H), 7.11(dd, 1H), 7.15–7.35(complex m, 3H), 7.78(td, 2H), 8.33(d, 1H); and (Example 7A): Methyl 4-[(2-butyl-1H-benzimidazol-1-yl)methyl]-3-nitrobenzoate, as an oil, NMR (CDCl$_3$): 0.90(t, 3H), 1.43(m, 2H), 1.83(m, 2H), 2.78(t, 2H), 3.95(s, 3H), 5.80(s, 2H), 6.56(d, 1H), 7.05(dd, 1H), 7.25(m, 2H), 7.83(dd, 1H), 8.06(dd, 1H), 8.85(d, 1H).

The following bromomethyl compounds used in Examples 5A, 6A and 7A were obtained from the correspondingly substituted methyl 4-methyl benzoates using an analogous procedure to that described in Example 1, part (iii), in yields ranging from 30–90%:

(Example 5C): Methyl 2-bromo-4-bromomethylbenzoate, as an oil; NMR (CDCl$_3$): 3.94(s, 3H), 4.41(s, 2H), 7.37(dd, 1H), 7.69(d, 1H), 7.76(d, 1H);

(Example 6C): Methyl 3-bromo-4-bromomethylbenzoate, as a white solid; m.p. 57°–59° C.; NMR (CDCl$_3$): 3.93(s, 3H), 4.60(s, 2H), 7.53(d, 1H), 7.95(dd, 1H), 8.24(d, 1H); and (Example 7C): Methyl 3-nitro-4-bromomethylbenzoate, as an oil; NMR (CDCl$_3$): 3.98(s, 3H), 4.85(s, 2H), 7.68(d, 1H), 8.25(dd, 1H), 8.66(d, 1H).

The 4-methylbenzoate esters used in Examples 5C, 6C and 7C, were either obtained commercially or were prepared by standard acid-catalysed esterification of the appropriate benzoic acid.

EXAMPLE 8

Using an analogous procedure to that described in Example 2, methyl-4-[(2-butyl-1H-benzimidazol-1-yl)methyl]-2-methylbenzoate (A) (400 mg) was hydrolysed to give 4-[(2-butyl-1H-benzimidazol-1-yl)methyl]-2-methylbenzoic acid (310 mg), as a white solid, m.p. 191°–192° C. (from aqueous methanol); NMR (d$_6$-DMSO): 0.86(t, 3H), 1.35(m, 2H), 1.70(m, 2H), 2.45(s, 3H), 2.82(t, 2H), 5.49(s, 2H), 6.88(d, 1H), 7.04(s, 1H), 7.05–7.2(complex m, 2H), 7.3–7.65(complex m, 2H), 7.75(d, 1H), 12.7(br s, 1H); mass spectrum (−ve FAB, DMSO/glycerol): 321 (M−H)$^-$, 173; microanalysis found: C, 73.5; H, 6.9; N, 8.6; C$_{20}$H$_{22}$N$_2$O$_2$.0.25H$_2$O requires: C, 73.7; H, 6.9; N, 8.3%.

The starting material (A) was obtained as follows:

(i) N-Bromosuccinimide (19.6 g) and azo(-bisisobutyronitrile) (200 mg) were added to a solution of 2,6-dimethylbenzoic acid in carbon tetrachloride (300 ml) and chloroform (50 ml). The mixture was degassed, placed under an atmosphere of argon and then heated under reflux for 2 hours. The mixture was cooled to ambient temperature and insoluble material removed by filtration. The filtrate was then extracted with aqueous sodium bicarbonate solution and the aqueous extracts carefully acidified with 48% hydrobromic acid. The precipitated solid was collected by filtration and dried under vacuum to give 4-bromomethyl-2-methylbenzoic acid (B) (3.92 g) as a white solid, m.p. 157°–160° C.; NMR (CDCl$_3$): 2.66(s, 3H), 4.56(s, 2H), 7.2–7.35(complex m, 2H), 8.04(d, 1H).

(ii) Oxalyl chloride (2.3 ml) was added to a solution of compound (B) (3.9 g) and DMF (0.3 ml) in dry dichloromethane (100 ml) and the mixture was stirred for 3 hours. The solvent and excess oxalyl chloride were removed by evaporation and dry methanol (50 ml) was added to the residue. The mixture was then stirred for 2 hours and the solvent removed by evaporation. The residue was partitioned between dichloromethane and aqueous sodium bicarbonate solution. The organic layer was separated, dried (MgSO4) and evaporated. The residue was triturated with a mixture of hexane and ether to give methyl 4-bromomethyl-2-methylbenzoate (C) (3.51 g) as a white solid, m.p. 51°–53° C.; NMR (CDCl$_3$): 2.59 (s, 3H), 3.89 (s, 3H), 4.44(s, 2H), 7.2–7.3-(complex m, 2H), 7.88(d, 1H).

(iii) Using an analogous procedure to that described in Example 1, part (iii), but starting from methyl 4-bromomethyl-2-methylbenzoate (C) (608 mg) and proportionate quantities of other necessary reagents, there was obtained, after flash chromatography eluting with ethyl acetate/hexane (1:1 v/v), methyl 4-[(2-butyl-1H-benzimidazol-1-yl)methyl]-2-methylbenzoate (A) (408 mg) as an oil; NMR (CDCl$_3$): 0.92(t, 3H), 1.43(m, 2H), 1.83(m, 2H), 2.53(s, 3H), 2.85(t, 2H), 3.87(s, 3H), 5.34(s, 2H), 6.87(d, 1H), 6.93(s, 1H), 7.1–7.3(complex m, 3H), 7.79(d, 1H), 7.84(d, 1H).

EXAMPLE 9

A 1.6M solution of butyllithium in hexane (0.70 ml) was added dropwise to a solution of 2-butyl-1-[(4-bromo-2-fluorophenyl)methyl]benzimidazole (A) (361 mg) in dry THF (3 ml) under an atmosphere of argon at −78° C. The mixture was stirred at −78° C. for 20 minutes, then dry carbon dioxide was bubbled through the solution for 30 minutes allowing the mixture to warm to 0° C. The mixture was then stirred at ambient temperature for 15 hours. The solvent was evaporated, and the residue extracted with 0.1M aqueous sodium hydroxide solution. The resulting solution was acidified with 20% aqueous citric acid solution. The resultant precipitate was collected and dried under vacuum to give 4-[(2-butyl-1H-benzimidazol-1-yl)methyl]-3-fluorobenzoic acid (65 mg) as a white solid, m.p. 224°–226° C.; NMR (d$_6$-DMSO): 0.87(t, 3H), 1.37(m, 2H), 1.71(m, 2H), 2.82(t, 2H), 5.60(s, 2H), 6.89(t, 1H), 7.05–7.25(m, 2H), 7.35–7.8(complex m, 4H), 13.2(br s, 1H); mass spectrum (−ve FAB, DMSO/glycerol): 325 (M−H)$^-$, 281, 173; microanalysis found: C, 69.8; H, 6.2; N, 8.2; $C_{19}H_{19}FN_2O_2$ requires C, 69.9; H, 5.9; N, 8.6%.

The starting material (A) was obtained as follows:

Using an analogous procedure to that described in Example 1, part (iii), but starting from 4-bromomethyl-3-fluoro-1-bromobenzene (1.77 g) and proportionate quantities of the other necessary reagents, there was obtained, after flash chromatography eluting with ethyl acetate/hexane (1:1 v/v), 2-butyl-1-[(4-bromo-2-fluorophenyl)methyl]benzimidazole (A) (1.57 g) as a white solid, m.p. 111°–113° C.; NMR (CDCl$_3$): 0.93(t, 3H), 1.44(m, 2H), 1.83(m, 2H), 2.83(t, 2H), 5.32(s, 2H), 6.52(t, 1H), 7.1–7.4(complex m, 5H), 7.76(dd, 1H).

EXAMPLE 10

Using an analogous procedure to that described in Example 2, methyl 4-[(2-butyl-5,6-dichloro-1H-benzimidazol-1-yl)methyl]benzoate (A) (250 mg) was hydrolysed to give 4-[(2-butyl-5,6-dichloro-1H-benzimidazol-1-yl)methyl]benzoic acid (190 mg) as a white solid, m.p. 244°–246° C. (from methanol/ethyl acetate); NMR (d$_6$-DMSO): 0.84(t, 3H), 1.32(m, 2H), 1.67(m, 2H), 2.79(t, 2H), 5.60(s, 2H), 7.15(d, 2H), 7.85(s, 2H), 7.89(d, 2H), 12.9(br s, 1H); mass spectrum (−ve FAB, DMSO/glycerol): 375 (M−H)$^-$, 241; microanalysis found: C, 60.2; H, 4.5; N, 7.0; $C_{19}H_{18}Cl_2N_2O_2$ requires: C, 60.5; H, 4.8; N, 7.4%.

The starting material (A) was obtained as follows:

Using an analogous procedure to that described in Example 1, (part iii), but starting from 2-butyl-5,6-dichlorobenzimidazole (495 mg) (prepared from 4,5-dichloro-1,2-phenylenediamine by the method of M. A. Phillips in *J. Chem. Soc.*, (1928), 2393; m.p. 145°–148° C.) and methyl 4-bromomethylbenzoate (465 mg), together with proportionate quantities of other necessary reagents, there was obtained, after flash chromatography eluting with ethyl acetate/hexane (2.5:1 v/v), methyl 4-[(2-butyl-5,6-dichloro-1H-benzimidazol-1-yl)methyl]benzoate (A) (275 mg) as a white solid, m.p. 140°–142° C. (from hexane/ethyl acetate); NMR (CDCl$_3$): 0.92(t, 3H), 1.41(m, 2H), 1.81(m, 2H), 2.80(t, 2H), 3.91(s, 3H), 5.33(s, 2H), 7.07(d, 2H), 7.24(s, 1H), 7.84(s, 1H), 8.01(d, 2H).

EXAMPLE 11

Using an analogous procedure to that described in Example 2, methyl 4-[(2-butyl-5-fluoro-1H-benzimidazol-1-yl)methyl]benzoate (A) (140 mg) was hydrolysed to give 4-[(2-butyl-5-fluoro-1H-benzimidazol-1-yl)methyl]benzoic acid (90 mg) as a white solid, m.p. 202°–204° C. (from aqueous methanol); NMR (d$_6$-DMSO): 0.85(t, 3H), 1.34(m, 2H), 1.68(m, 2H), 2.80(t, 2H), 5.57(s, 2H), 7.00(td, 1H), 7.16(d, 2H), 7.3–7.5(complex m, 2H), 7.88(d, 2H), 12.9(br s, 1H); mass spectrum (−ve FAB, DMSO/glycerol): 325 (M−H)$^-$, 191; microanalysis found: C, 69.3; H, 5.8; N, 8.5; $C_{19}H_{19}FN_2O_2.025$ H$_2$O requires: C, 69.0; H, 5.9; N, 8.5%.

The starting material (A) was obtained as follows:

(i) A mixture of methyl 4-aminomethylbenzoate (0.50 g) (obtained by acid-catalysed esterification of 4-aminomethylbenzoic acid), 2,5 difluoronitrobenzene (0.40 g) and potassium carbonate (0.35 g) in DMF (5 ml) was heated at 100° for 5 hours. The mixture was cooled, dichloromethane (20 ml) was added and insoluble material was removed by filtration. The solvent was evaporated and the residue recrystallised from methanol/ethyl acetate to give methyl 4-N-(4-fluoro-2-nitrophenyl)aminomethylbenzoate (B) (0.54 g) as orange needles, m.p. 144°–146° C.; NMR (CDCl$_3$): 3.92(s, 3H), 4.61(d, 2H), 6.70(dd, 1H), 7.17(ddd, 1H), 7.62(d, 2H), 7.93(dd, 1H), 8.04(d, 2H), 8.36(br s, 1H); microanalysis found: C, 59.0; H, 4.1; N, 9.0; $C_{15}H_{13}FN_2O_4$ requires: C, 59.2; H, 4.3; N, 9.2%.

(ii) A mixture of powdered tin (II) chloride dihydrate (1.0 g) and the nitro compound (B) (266 mg) in methanol (7 ml) was heated under reflux for 10 hours. The solvent was evaporated and ethyl acetate (20 ml) and 1M aqueous sodium hydroxide solution (15 ml) added to the residue. The mixture was filtered through diatomaceous earth, the aqueous layer was separated and extracted with ethyl acetate (2×20 ml). The combined extracts were washed with brine (20 ml), dried (MgSO$_4$) and evaporated. The crude diamine residue was then dissolved in toluene (7 ml) and valeric anhydride (0.2 ml), valeric acid (0.1 ml) and p-toluenesulphonic acid monohydrate (190 mg) added. The mixture was heated under reflux for 10 hours. Ethyl acetate (20 ml) was added and the solution extracted with aqueous sodium bicarbonate solution. The organic phase was dried (MgSO$_4$) and evaporated. The residue was purified by flash chromatography, eluting with triethylamine/ethyl acetate/hexane (1:40:60), to give methyl 4-[(2-butyl-5-fluoro-1H-benzimidazol-1-yl)methyl]benzoate (A) (142 mg) as an oil, NMR (CDCl$_3$): 0.91(t, 3H), 1.41(m, 2H), 1.81(m, 2H), 2.81(t, 2H), 3.90(s, 3H), 5.37(s, 2H), 6.85–7.05(complex m, 2H), 7.08(d, 2H), 7.44(dd, 1H).

EXAMPLES 12 AND 13

The following compounds were prepared using an analogous procedure to that described in Example 11 in yields ranging from 52–85%:

(Example 12): 4-[(2-butyl-6-fluoro-1H-benzimidazol-1-yl)methyl]benzoic acid, as a white solid, m.p. 202°–204° C. (from aqueous methanol); NMR (d$_6$-DMSO): 0.84(t, 3H), 1.33(m, 2H), 1.67(m, 2H), 2.77(t, 2H), 5.55(s, 2H), 6.99(td, 1H), 7.17(d, 2H), 7.35(dd, 1H), 7.58(dd, 1H), 7.89(d, 2H); mass spectrum (−ve FAB, DMSO/glycerol): 325(M−H)$^-$, 191; microanalysis found: C, 69.5; H, 5.9; N, 8.3; $C_{19}H_{19}FN_2O_2$ requires: C, 69.9; H, 5.9; N, 8.6%; and (Example 13): 4-[(2-butyl-5-trifluoromethyl-1H-benzimidazol-1-yl)methyl]benzoic acid, as a white solid, m.p. 254°–256° C. (from aqueous methanol); NMR ($d_6$-DMSO): 0.85(t, 3H), 1.35(m, 2H), 1.70(m, 2H), 2.85(t, 2H), 5.66(s, 2H), 7.18(d, 2H), 7.49(dd, 1H), 7.66(d, 1H), 7.90(d, 2H), 7.96(d, 1H), 12.9(br s, 1H); mass spectrum (−ve FAB, DMSO/glycerol): 375 $(M-H)^-$, 241; microanalysis found: C, 63.9; H, 5.1; N, 7.5; $C_{20}H_{19}F_3N_2O_2$ requires C, 63.8; H, 5.1; N, 7.4%.

The following starting materials were obtained using an analogous procedure to that described in Example 11, part (ii), in yields ranging from 33–67%:

(Example 12A): methyl 4-[(2-butyl-6-fluoro-1H-benzimidazol-1-yl)methyl]benzoate, as an oil; NMR ($CDCl_3$): 0.92(t, 3H), 1.42(m, 2H), 1.83(m, 2H), 2.88(t, 2H), 3.91(s, 3H), 5.36(s, 2H), 6.85(dd, 1H), 7.04(td, 1H), 7.10(d, 2H), 7.75(dd, 1H), 8.00(d, 2H); and (Example 13A): methyl 4-[(2-butyl-5-trifluoromethyl-1H-benzimidazol-1-yl)methyl]benzoate, as an oil, NMR ($CDCL_3$): 0.93(t, 3H), 1.42(m, 2H), 1.83(m, 2H), 2.86(t, 2H), 3.91(s, 3H), 5.42(s, 2H), 7.09(d, 2H), 7.23(d, 1H), 7.45(d, 1H), 8.00(d, 2H), 8.05(s, 1H).

The following starting materials used in Examples 12A and 13A were obtained using an analogous procedure to that described in Example 11, part (i), in yields ranging from 61–81%:

(Example 12B): methyl 4-N-(5-fluoro-2-nitrophenyl)aminomethylbenzoate, as yellow needles, m.p. 132°–133° C. (from hexane/ethyl acetate); NMR ($CDCl_3$): 3.93(s, 3H), 4.58(d, 2H), 6.3–6.5(complex m, 2H), 7.42(d, 2H), 8.06(d, 2H), 8.25(dd, 1H), 8.58(br s, 1H); microanalysis found: C, 58.9; H, 4.1; N, 9.0; $C_{15}H_{13}FN_2O_4$ requires: C, 59.2; H, 4.3; N, 9.2%; and (Example 13B): methyl 4-N-(2-nitro-4-trifluoromethylphenyl)aminomethylbenzoate, as yellow needles, m.p. 84°–86° C. (from aqueous methanol); NMR ($CDCl_3$): 3.92(s, 3H), 4.66(d, 2H), 6.83(d, 1H), 7.41(d, 2H), 7.56(d, 1H), 8.05(d, 2H), 8.50(s, 1H), 8.68(br s, 1H); microanalysis found: C, 54.3; H, 3.5; N, 7.7; $C_{16}H_{13}F_3N_2O_4$ requires: C, 54.2, H, 3.7; N, 7.9%.

EXAMPLE 14

Using an analogous procedure to that described in Example 2, methyl 4-[(2-hexyl-1H-benzimidazol-1-yl)methyl]benzoate (A) (300 mg) was hydrolysed to give 4-[(2-hexyl-1H-benzimidazol-1-yl)methyl]benzoic acid (195 mg), as a white solid, m.p. 191°–193° C. (from ethyl acetate/methanol); NMR ($d_6$-DMSO/$d_4$-acetic acid): 0.82(t, 3H), 1.1–1.4(complex m, 6H), 1.70(m, 2H), 2.86(t, 2H), 5.58(s, 2H), 7.1–7.3(complex m, 4H), 7.42(m, 1H), 7.64(m, 1H), 7.92(d, 2H); mass spectrum (+ve CI): 337 $(M+H)^+$; microanalysis found: C, 75.2; H, 7.5; N, 8.4; $C_{21}H_{26}N_2O_2$ requires C, 75.0; H, 7.1; N, 8.3%.

The starting material (A) was obtained as follows:

(i) Using an analogous procedure to that described in Example 11, part (i), but starting from 2-fluoronitrobenzene (14.1 g) and proportionate quantities of other necessary reagents, there was obtained methyl 4-N-(2-nitrophenyl)aminomethylbenzoate (B) (30.48 g) as orange needles, m.p. 113°–116° C. (from methanol); NMR ($d_6$-DMSO): 3.84(s, 3H), 4.72(d, 2H), 6.68(m, 1H), 6.83(d, 1H), 7.42(m, 1H), 7.50(d, 2H), 7.93(d, 2H), 8.09(dd, 1H), 8.70(br t, 1H); microanalysis found: C, 62.9; H, 5.1; N, 9.8; $C_{15}H_{14}O_4N_2$ requires: C, 62.9; H, 4.9; N, 9.8%.

(ii) A solution of the nitroamine (B) (7.0 g) in dry THF (100 ml) was added to platinum (IV) oxide (400 mg). The mixture was then stirred under hydrogen at atmospheric pressure for 16 hours. The catalyst was removed by filtration and the filtrate evaporated to give methyl 4-[N-(2-aminophenyl)aminoethyl]benzoate (C) (5.79 g) as an oil; NMR ($CDCl_3$): 3.4(br s, 3H); 3.90(s, 3H); 4.38(s, 2H); 6.5–6.85(complex m, 4H); 7.44(d, 2H); 8.00(d, 2H).

(iii) Trifluoromethylsulphonyl anhydride (0.8 ml) was added dropwise to a stirred solution of triphenylphosphine oxide (2.8 g) in dry dichloromethane (20 ml) at 0° under an atmosphere of nitrogen. The mixture was stirred at 0° C. for 20 minutes and then a solution of the diamine (C) (0.5 g) and heptanoic acid (0.36 ml) in dry dichloromethane (10 ml) was added dropwise. The mixture was stirred for a further 1 hour at 0° C. Saturated aqueous sodium bicarbonate solution (20 ml) was added, the phases separated and the aqueous layer extracted with dichloromethane (100 ml). The combined extracts were dried ($MgSO_4$) and evaporated. The residue was dissolved in ether and insoluble material removed by filtration. The filtrate was evaporated and the residue purified by flash chromatography eluting with hexane/ethyl acetate (3:2 v/v) to give methyl 4-[(2-hexyl-1H-benzimidazol-1yl)methyl]benzoate (A) (325 mg) as an oil, NMR ($CDCl_3$): 0.86(t, 3H); 1.1–1.5(complex m, 6H); 1.82(m, 2H); 2.81(t, 2H); 3.90(s, 3H); 5.39(s, 2H); 7.10(d, 2H); 7.1–7.4(complex m, 3H); 7.78(dd, 1H), 7.98(d, 2H).

EXAMPLE 15

Using an analogous procedure to that described in Example 2, methyl 4-[(2-propyl-1H-benzimidazol-1-yl)methyl]benzoate [obtained by heating at reflux for 90 minutes a mixture of methyl 4-N-(2-propionylaminophenyl)aminomethylbenzoate (A) (1.1 g) and acetic acid (25 ml), followed by removal of volatile material by evaporation] was hydrolysed to give, after flash chromatography eluting with dichloromethane/methanol (19:1 v/v), 4-[(2-propyl-1H-benzimidazol-1-yl)methyl]benzoic acid (0.58 g) as a white solid, m.p. 208°–210° C.; NMR ($d_6$-DMSO/$d_4$-acetic acid): 0.94(t, 3H); 1.76(m, 2H); 2.84(t, 3H); 5.59(s, 2H); 7.1–7.3(complex m, 4H); 7.42(m, 1H); 7.63(m, 1H); 7.91(d, 2H); mass spectrum (−ve FAB, DMSO/glycerol): 293$(M-H)^-$; microanalysis found: C, 72.7; H, 6.1; N, 9.5; $C_{18}N_{18}N_2O_2$. 0.2 $H_2O$ requires C, 72.6; H, 6.1; N, 9.4%.

The starting material (A) was obtained as follows:

A mixture of butyric acid (1.0 ml), 4-[-N-(2-aminophenyl)aminomethyl]benzoate (1.5 g), dicyclohexylcarbodiimide (1.3 g) and 1-hydroxy-bezotriazole (1.0 g) in dry chloromethane (10 ml) was stirred for 18 hours. The mixture was filtered and the filtrate washed with saturated aqueous sodium bicarbonate solution, brine, then dried ($Na_2SO_4$) and evaporated. The residue was purified by flash chromatography eluting with ether/hexane (2:1 v/v) to give methyl 4-N-(2-propionylaminophenyl)aminomethylbenzoate (A) (1.33 g) as a white solid, m.p. 132°–134° C.; NMR ($CDCl_3$): 1.01(t, 3H); 1.77(m, 2H); 2.38(t, 2H); 3.90(s, 3H); 4.40(s, 2H); 6.05–6.8(complex m, 2H); 7.0–7.25(complex m, 2H); 7.43(d, 2H); 8.00(d, 2H).

EXAMPLES 16–18

The following compounds were obtained by an analogous procedure to that described in Example 3, but using the appropriate sulphonamide, except that the hydrochloric acid wash in the work-up procedure was omitted, in yields ranging from 24–53%:

(Example 16): 4-[(2-butyl-1H-benzimidazol-1-yl)methyl]-N-methylsulphonyl benzamide, as a white solid, m.p. 105°–117° C. (decomposition), NMR (d$_6$-DMSO): 0.86(t, 3H); 1.35(m, 2H); 1.70(m, 2H); 2.80(t, 2H); 2.85(s, 3H); 5.50(s, 2H); 7.05(s, 2H); 7.1–7.2(complex m, 2H); 7.35–7.45(m, 1H); 7.55–7.65(m, 1H); 7.87(d, 2H); mass spectrum (−ve FAB, DMSO/glycerol) 384 (M−H)$^-$, 211, 173;

(Example 17): 4-[(2-butyl-1H-benzimidazol-1-yl)methyl]-N-phenylsulphonyl-3-nitrobenzamide, as a white solid, m.p. 121°–125° C. (from ethyl acetate); NMR (CDCl$_3$): 0.90(t, 3H); 1.42(m, 2H); 1.80(m, 2H); 2.77(t, 2H); 5.75(s, 2H); 7.05(d, 1H); 7.1–7.5(complex m, 7H); 8.01(dd, 2H); 8.16(dd, 1H); 8.94(d, 1H); mass spectrum (−ve FAB, DMSO/m-nitrobenzyl alcohol): 491(M−H)$^-$; 475, 458, 173; microanalysis found: C, 61.6; H, 5.2; N, 12.8; C$_{25}$H$_{24}$N$_4$O$_5$S. 0.5 (dimethylaminopyridine) requires C, 61.8; H, 5.2; N, 12.7%;

(Example 18): 4-[(2-butyl-1H-benzimidazol-1-yl)methyl]-N-(2-methylphenyl)sulphonylbenzamide, as a white solid, m.p. 194°–195° C. (from aqueous ethanol); NMR (d$_6$-DMSO): 0.88(t, 3H); 1.37(m, 2H); 1.72(m, 2H); 2.13(s, 3H); 2.59(s, 3H); 2.83(t, 2H); 5.48(s, 2H); 6.87(d, 1H); 7.02(s, 1H); 7.1–7.65(complex, 8H); 7.99(d, 1H); 12.66(br s, 1H); mass spectrum (+ve FAB, DMSO/glycerol): 476 (M+H)+; microanalysis found: C, 67.7; H, 5.9; N, 8.5; C$_{27}$H$_{29}$N$_3$O$_3$S requires: C, 68.2; H, 6.1; N, 8.8%.

EXAMPLE 19

(Note: all parts by weight)

The compounds of the invention may be administered for therapeutic or prophylactic use to warm-blooded animals such as man in the form of conventional pharmaceutical compositions, typical examples of which include the following:

| a) Capsule (for oral administration) | |
|---|---|
| Active ingredient* | 20 |
| Lactose powder | 578.5 |
| Magnesium stearate | 1.5 |
| b) Tablet (for oral administration) | |
| Active ingredient* | 50 |
| Microcrystalline cellulose | 400 |
| Starch (pregelatinised) | 47.5 |
| Magnesium stearate | 2.5 |
| c) Injectable Solution (for intravenous administration) | |
| Active ingredient* | 0.05–1.0 |
| Propylene glycol | 5.0 |
| Polyethylene glycol (300) | 3.0–5.0 |
| Purified water | to 100% |
| d) Injectable Suspension (for intramuscular administration) | |
| Active ingredient* | 0.05–1.0 |
| Methylcellulose | 0.5 |
| Tween 80 | 0.05 |
| Benzyl alcohol | 0.9 |
| Benzalkonium chloride | 0.1 |
| Purified water | to 100% |

Note:
the active ingredient* may typically be an Example described hereinbefore and will conveniently be present as a pharmaceutically acceptable acid-addition salt, such as the hydrochloride salt. Tablets and capsules formulations may be coated in conventional manner in order to modify or sustain dissolution of the active ingredient. Thus, for example, they may be coated with a conventional enterically digestible coating.

Chemical Formulae

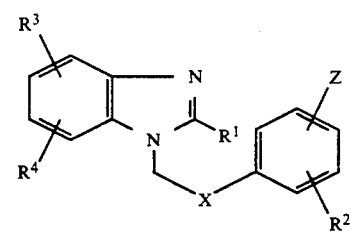

I

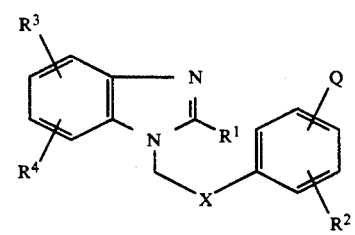

II

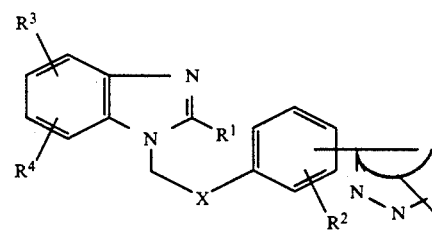

III

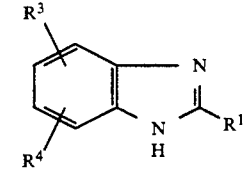

IV

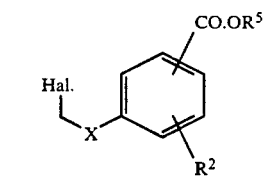

V

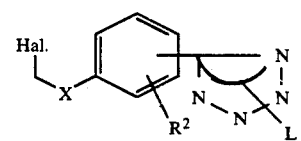

VI

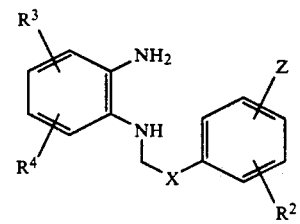

VII

-continued
Chemical Formulae
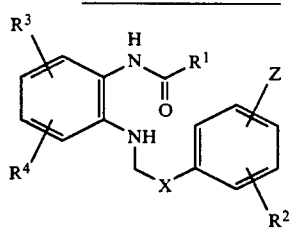
VIII
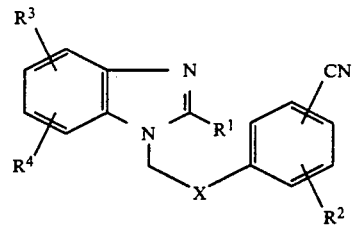
IX
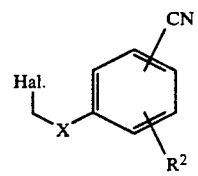
X
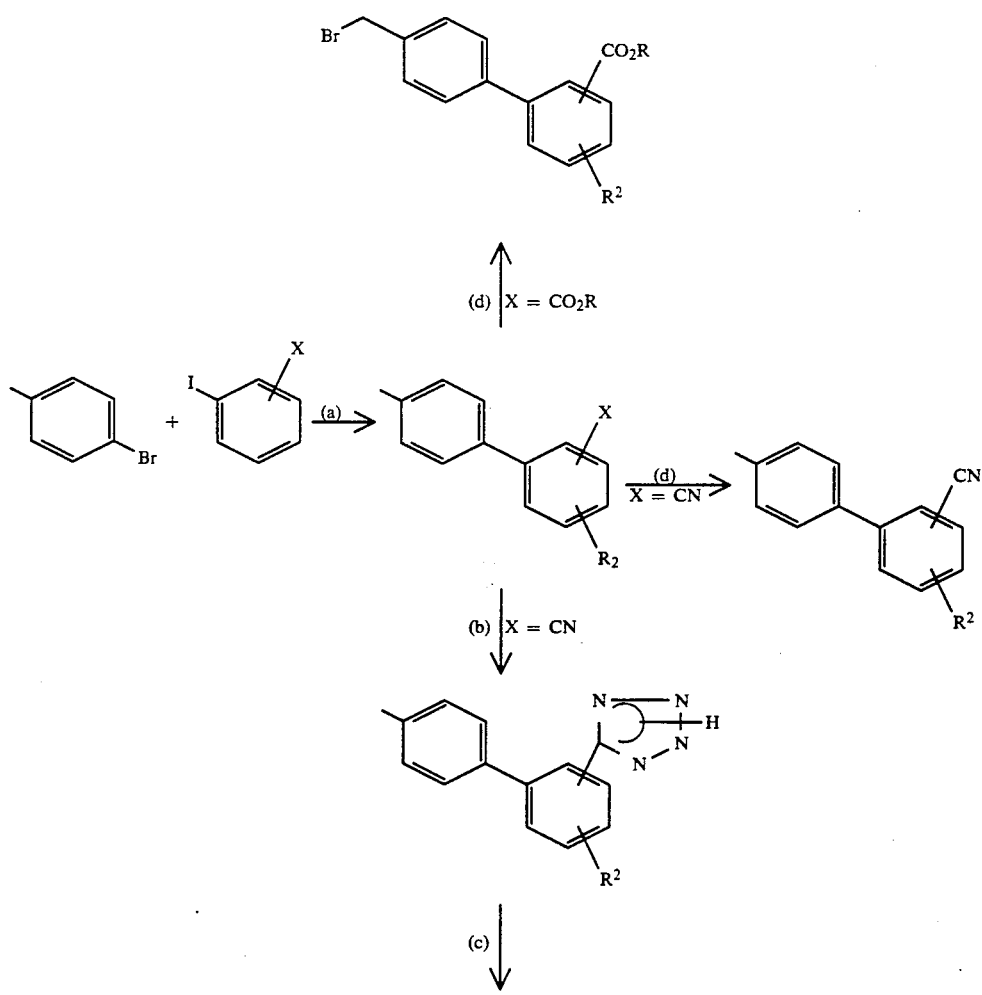
Scheme 1

Scheme 1 -continued

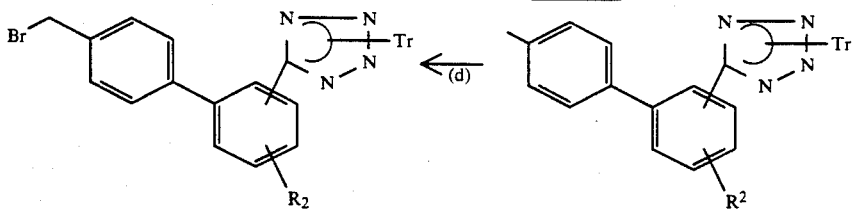

Note:
R = lower alkyl, benzyl, phenyl; Tr = triphenylmethyl (trityl)
Reagents:
(a) BuLi/THF; ZnCl$_2$/Et$_2$O; Pd(Ph$_3$P)$_4$
(b) Bu$_3$Sn.N$_3$/toluene; HCl/toluene
(c) Tr.Cl/Et$_3$N/CH$_2$Cl$_2$
(d) N-bromosuccinimide/azoisobutyronitrile/CCl$_4$

What we claim is:

1. A benzimidazole derivative of the formula I

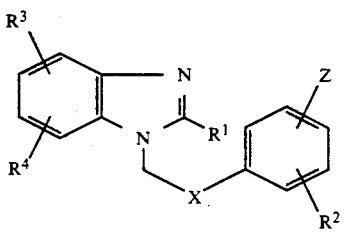

wherein $R^1$ is (1-8C)alkyl, (3-8C)cycloalkyl-(1-4C)alkyl, phenyl or phenyl (1-4C)alkyl; $R^2$ is hydrogen, (1-4C)alkyl, (1-4C)alkoxy, halogeno, trifluoromethyl, cyano or nitro; $R^3$ $R^4$ are independently selected from hydrogen, (1-4C)alkyl, (1-4C)alkoxy, halogeno, trifluoromethyl, cyano and nitro; X is a direct bond between the adjacent phenyl and methylene moieties; and Z is 1H-tetrazol-5-yl or a group of the formula —CO.OR$^5$ or —CO.NH.SO$_2$.R$^6$ is which $R^5$ is hydrogen or a residue of a physiologically acceptable alcohol or phenol of formula R$^5$OH which forms a non-toxic, biodegradable ester, and $R^6$ is (1-6C)alkyl, (3-8C)cycloalkyl or phenyl; and wherein any of said phenyl moieties may be unsubstituted or bear one or two substituents independently selected from (1-4C)alkyl, (1-4)alkoxy, halogeno, cyano and trifluoromethyl; or a physiologically acceptable salt thereof except when $R^5$ is other than hydrogen.

2. A compound as claimed in claim 1 wherein $R^1$ is methyl, ethyl, propyl, butyl, isobutyl, sec-butyl, pentyl, hexyl, cyclopropyl, cyclopentyl, cyclohexyl, cyclopropylmethyl, cyclopentylmethyl, cyclohexylmethyl, 2-cyclopentyl-ethyl, phenyl, benzyl, 1-phenylethyl or 2-phenylethyl; $R^2$ is hydrogen, methyl, ethyl, methoxy, ethoxy, fluoro, chloro, bromo, iodo, trifluoromethyl, cyano or nitro; $R^3$ and $R^4$ are independently selected from hydrogen, methyl, ethyl, methoxy, ethoxy, fluoro, chloro, bromo, iodo, trifluoromethyl, cyano, and nitro; $R^5$ is hydrogen or a residue derived from a (1-6C)alkanol, phenol or glycerol; and $R^6$ is methyl, ethyl, propyl, isopropyl, butyl, pentyl, cyclobutyl, cyclopentyl, cyclohexyl or phenyl; and wherein any of said phenyl moieties may be unsubstituted or bear one or two substituents independently selected from methyl, ethyl, methoxy, ethoxy, fluoro, chloro, bromo, cyano and trifluoromethyl.

3. A compound as claimed in claim 1 or 2 wherein $R^1$ is (1-8C)alkyl; $R^2$ is hydrogen, (1-4C)alkyl, halogeno or nitro; $R^3$ and $R^4$ are independently selected from hydrogen, halogeno and trifluoromethyl; and Z is selected from 1H-tetrazol-5-yl, carboxy and a group of the formula —CO.NH.SO$_2$.R$_6$ in which $R^6$ is (1-6C)alkyl, (3-8C)cycloalkyl or phenyl; and wherein Z is attached at the 2- or 4-position relative to X; or a physiologically acceptable salt thereof.

4. A coumpoud as claimed in claim 1 wherein Z is attached at the 4-position relative to X.

5. A compound as claimed in claim 1 wherein $R^1$ is butyl.

6. A compound of the formula I selected from
4-[(2-butyl- 1H-benzimidazol-1-yl) methyl]-N-phenyl-sulphonylbenzamide;
4-[(2-butyl-1H-benzimidazol-1)methyl]-2-bromobenzoic acid;
4-[(2-butyl-1H-benzimidazol-1-yl)methyl]-N-(2-methylphenyl)suphonylbenzamide; or a physiologically acceptable salt thereof.

7. A salt as claimed in claim 1 which is selected from alkali metal, alkaline earth metal, aluminum and ammonium salts, and from salts with organic bases affording physiologicallly acceptable cations.

8. A pharmaceutical composition which comprises a compound of the formula I, or a physiologically acceptable salt thereof, as claimed in claim 1, together with a pharmaceutically acceptable diluent or carrier.

9. A method for antagonising one or more of the actions of angiotensis II in a warm-blooded animal requiring such treatment which comprises administering to said animal an antagonistically effective amount of a compound of formula I, or a physiologically acceptable salt thereof, as defined in claim 1.

10. A compound of the formula III

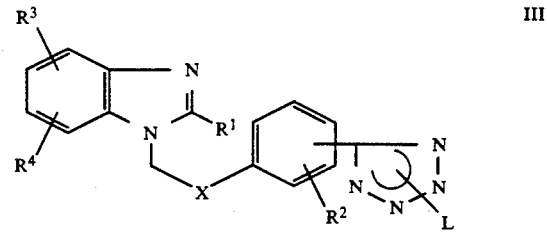

wherein $R^1$, $R^2$, $R^3$, $R^4$ and X have any of the values defined in claim 1, and L is a suitable protecting group for a nitrogen of the tetrazolyl moiety.

11. A compound as claimed in claim 10 wherein L is trityl, benzhydryl, trialkyltin or triphenyltin.

12. A compound as claimed in claim 11 wherein L is trimethyltin.

* * * * *